United States Patent
Felton et al.

(12) 
(10) Patent No.: US 6,303,326 B1
(45) Date of Patent: Oct. 16, 2001

(54) INSECT SALIVARY ENZYME TRIGGERS SYSTEMIC RESISTANCE

(75) Inventors: Gary W. Felton, Fayetteville, AR (US); Mary C. Mathews, Mashall, MO (US); Jianlong Bi, Riverside, CA (US); John B. Murphy, Fayetteville, AR (US)

(73) Assignee: University of Arkansas, Little Rock, AR (US)

( * ) Notice: Subject to any disclaimer, the term of this patent is extended or adjusted under 35 U.S.C. 154(b) by 0 days.

(21) Appl. No.: 09/205,630

(22) Filed: Dec. 3, 1998

Related U.S. Application Data

(60) Provisional application No. 60/067,457, filed on Dec. 4, 1997, now abandoned.

(51) Int. Cl.[7] .............................. C12Q 1/54; C12P 21/06; A23B 5/00
(52) U.S. Cl. ................... 435/14; 435/28; 435/39; 435/68.1; 435/183; 435/190; 435/805; 435/808; 435/814; 435/815; 436/95; 436/166; 436/169; 426/8; 426/9; 426/10; 426/12; 426/56; 426/57; 426/58; 514/2; 514/12
(58) Field of Search ................................ 435/14, 28, 39, 435/68.1, 183, 190, 805, 808, 814, 815; 436/95, 166, 169; 426/8, 9, 10, 12, 56, 57, 58; 514/12

(56) References Cited

U.S. PATENT DOCUMENTS

| | | | |
|---|---|---|---|
| 3,767,531 | 10/1973 | Olson et al. | 195/63 |
| 3,804,715 | 4/1974 | Sugimoto et al. | 195/31 |
| 4,557,927 | 12/1985 | Miyake et al. | 424/48 |
| 4,675,191 | 6/1987 | Villettaz | 426/10 |
| 4,929,451 | 5/1990 | Takenawa et al. | 426/10 |
| 4,957,749 | 9/1990 | Prieels et al. | 426/10 |
| 4,990,343 | 2/1991 | Haarasilta et al. | 426/10 |
| 4,996,062 | 2/1991 | Lehtonen et al. | 426/8 |
| 5,085,873 | 2/1992 | Degre | 426/8 |
| 5,094,951 | 3/1992 | Rosenberg | 435/190 |
| 5,304,468 | 4/1994 | Phillips et al. | 435/14 |

OTHER PUBLICATIONS

Gusui Wu et al., Activation of Host Defense Mechanisms by Elevated Production of $H_2O_2$ in Transgenic Plants, Plant Physiol. (1997) 115: 427–435.

Gusui Wu et al., Disease Resistance Conferred by Expression of a Gene Encoding $H_2O_2$–Generating Glucose Oxidase in Transgenic Potato Plants, The Plant Cell, vol. 7, 1357–1368, Sep. 1995.

P. Heiss et al., Cytotoxic Effect of Immunoconjugate Composed of Glucose Oxidase Coupled to a Chimeric Anti–ganglioside (GD2) Antibody on Spheroids (Meeting Abstract), National Cancer Institute, Anticancer Res. 1995; 15(6A):2438–9.

Coury Group Research, Research on Enzymatically–Amplified Sensors, pp. 1 and 2, 1997.

*Primary Examiner*—Christopher S. F. Low
*Assistant Examiner*—Abdel A. Mohamed
(74) *Attorney, Agent, or Firm*—Head, Johnson & Kachigian

(57) ABSTRACT

The present invention includes the characterization of the major salivary protein or enzyme of the corn earworm *Helicoverpa zea* for triggering resistance to bacterial blight and frogeye leafspot in soybeans and for triggering resistance to insects in tomatoes. The invention includes an enzyme or a novel protein secreted from the salivary glands of certain insects including the saliva of species belonging to the order Hymenoptera and Lepidoptera. The regurgitant of *Helocoverpa zea* obtained from the functional salivary glands contains a protein that possesses glucose oxidase activity. The amino acid sequence of the protein is unique and when the protein is applied to plants, it triggers disease and insect resistance systematically. The physical and kinetic attributes of the enzyme are a pH of 7.0, a pI of 4.4 and a molecular weight of 88 kd. The $k_m$ and $V_{max}$ of the enzyme for glucose is 26.9 mmol and 26.7 $\mu$mol min$^{-1}$ mg$^{-1}$, respectively. The enzyme may be expressed in crops for plant resistance and/or applied to crops for inhibiting foliar pathogens and/or other pests, in food applications for improving the shelf life or quality of the food products as well as the production of low alcohol products. Biomedical uses include using the enzyme for glucose monitoring of blood, urine, etc., as well as using the enzyme in the development of anti-cancer and/or anti-tumor agents and the production of antimicrobial products and the like. Various biochemical applications include the use of the enzyme in immunochemistry as well as for the enzymatic iodination of proteins and enzymatically amplified sensors for amperometry and voltammetry. Another use of the gene from the enzyme is an expression in a Baculovirus for pesticide usage.

8 Claims, 18 Drawing Sheets

FIG. 1

Insect Feeding Triggers Systemic Acquired Resistance Against *Cercospora sojina*

FIG. 5

Identification of the Source of Salivary Hydrogen Peroxide

| Treatment | Relative Activity |
|---|---|
| Media + Saliva | 100% |
| Media minus glucose + Saliva | 0% |

FIG. 8 Effect of Salivary Glucose Oxidase on Phytoalexins Systemic--[DAY 3]

FIG. 9 Effect of Salivary Glucose Oxidase on Phytoalexins Localized--[DAY 7]

Effect of Salivary Glucose Oxidase on Salicylic Acid
(Localized Effect)

Effect of Salivary Glucose Oxidase on Lipoxgenase Activity (Localized)

FIG. 13 Effect of Salivary Glucose Oxidase on Lipoxgenase Activity (Systemic)

FIG. 15

Salivary Glucose Oxidase Elicits Systemic Resistance to *Cercospora sojina*

FIG. 16

Salivary Glucose Oxidase Elicits Systemic
Resistance to *Pseudomonas syringae glycinea*

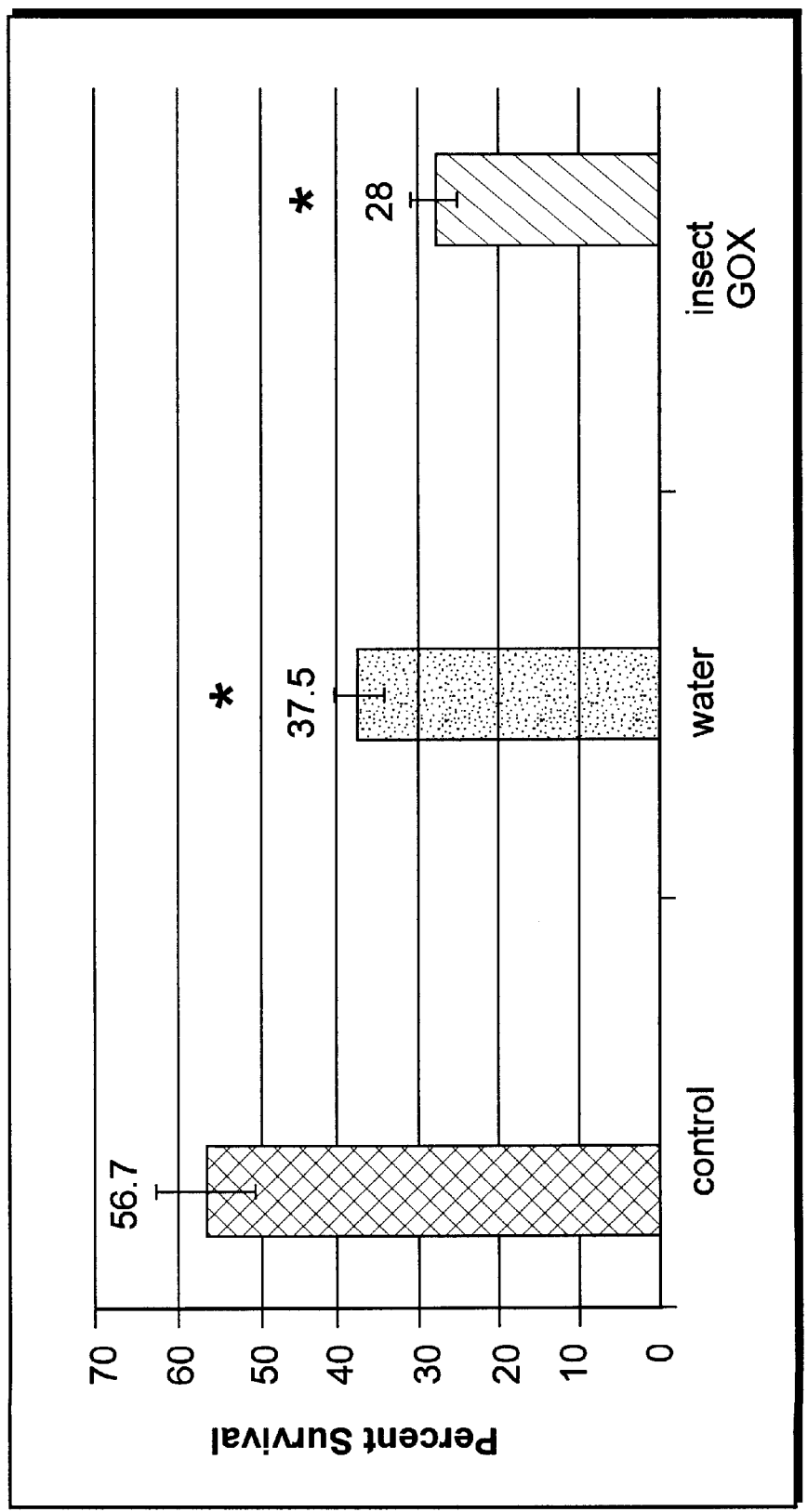
FIG. 17 Salivary Glucose Oxidase Triggers Systemic Resistance to *H. zea* in Tomato Leaves

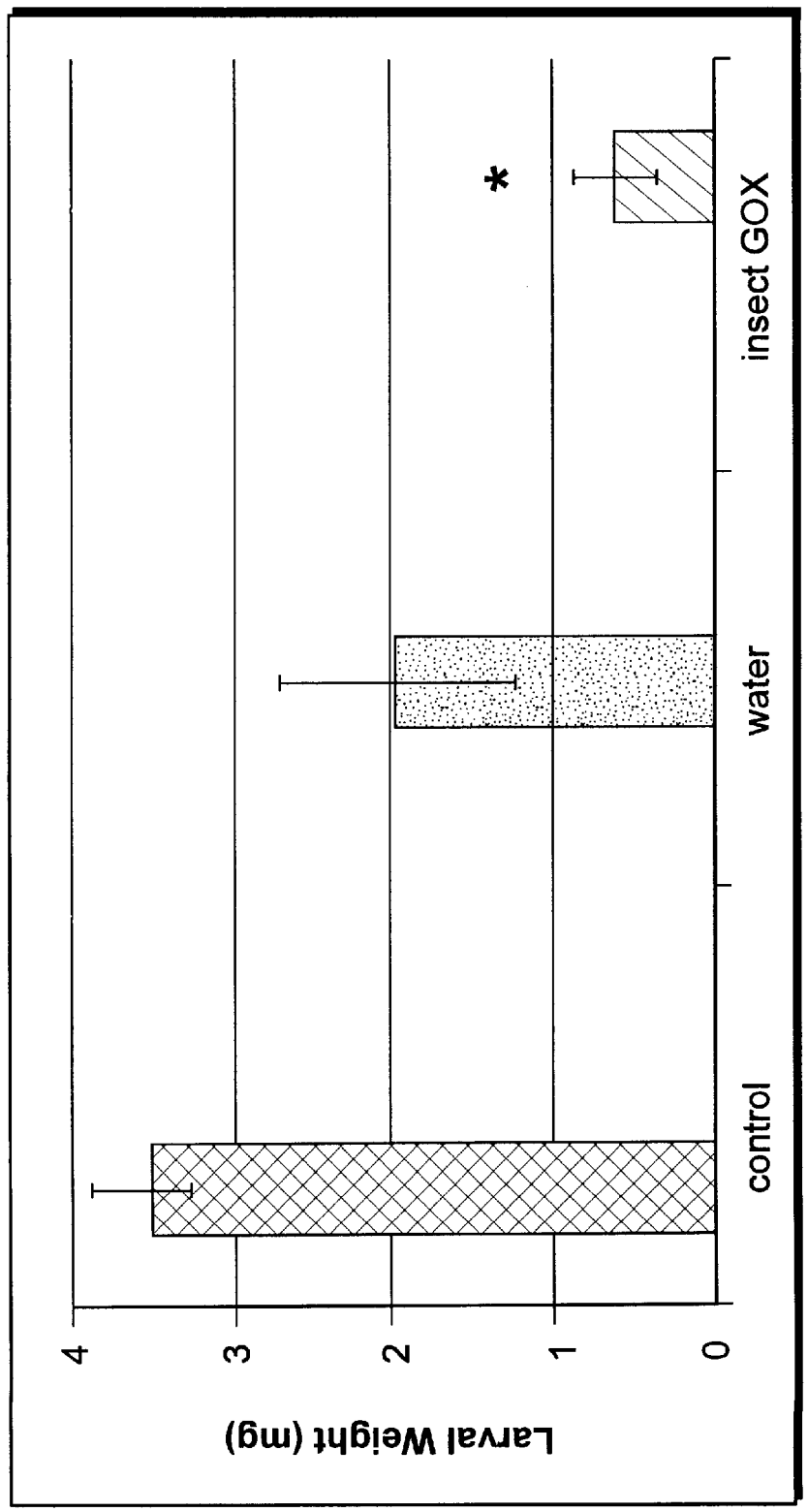
FIG. 18 Salivary Glucose Oxidase Triggers Systemic Resistance to *H. zea* in Tomato Leaves

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
       (A) LENGTH: 30 amino acid residues
       (B) TYPE: Amino acid sequence
       (C) STRANDEDNESS: Not Applicable
       (D) TOPOLOGY: Unknown (ii) MOLECULE TYPE: Protein
       (A) DESCRIPTION: The first 30 amino acids of the H. zea GOX were sequenced; unfortunately, all of the amino acids in the sequence could not be unambiguously assigned. The first 30 residues sequenced were as follows (iii) HYPOTHETICAL: No (iv) ANTI-SENSE: Not applicable (v) FRAGMENT TYPE: N-terminal fragment (vi) ORIGINAL SOURCE:
       (A) ORGANISM: Corn earworm
       (B) STRAIN: Helicoverpa zea
       (C) INDIVIDUAL ISOLATE: Salivary enzyme
       (D) DEVELOPMENTAL STAGE: Not applicable
       (E) HAPLOTYPE: Not applicable
       (F) TISSUE TYPE: Not applicable
       (G) CELL TYPE: Not applicable
       (H) CELL LINE: Not applicable
       (I) ORGANELLE: Not applicable (vii) IMMEDIATE SOURCE: Not applicable
       (A) LIBRARY: Not applicable
       (B) CLONE: Not applicable (viii) POSITION IN GENOME: Not applicable (ix) FEATURE:
       (A) NAME/KEY:
       (B) LOCATION: Not registered
       (C) IDENTIFICATION METHOD: Not completed
       (D) OTHER INFORMATION: Salivary enzyme of corn earworm H. zea having glucose oxidase (GOX) activity.

(x) PUBLICATION INFORMATION:
       (A) AUTHORS:
       (B) TITLE:
       (C) JOURNAL:
       (D) VOLUME:
       (E) ISSUE:
       (F) PAGES:
       (G) DATE:
       (H) DOCUMENT NUMBER:
       (I) FILING DATE:
       (J) PUBLICATION DATE:
       (K) RELEVANT RESIDUES IN SEQ ID NO:

(xi) SEQUENCE DESCRIPTION: SEQ ID NO: 1:

```
Met Ile Leu Ala Gln Gln Asp Xaa Gly Xaa Gln Thr Val Val Glu
1               5                   10                  15

Gly Ala Ser Ile Leu Asn Ser Xaa Thr Ala Xaa Val Xaa Thr Tyr
                20                  25                  30
```

INSECT SALIVARY ENZYME TRIGGERS SYSTEMIC RESISTANCE

CROSS REFERENCE TO RELATED APPLICATIONS

Priority is claimed to and this application is a continuation of U.S. patent application Ser. No. 60/067,457, filed Dec. 4, 1997, now abandoned.

BACKGROUND OF THE INVENTION

As will be appreciated by those skilled in the art, very little is understood about many of the complex interactions of insects and plants. For example, defoliation by soybean loopers triggers systemic acquired resistance to stem canker disease and redcrown rot (Russin et al., 1989; Padgett et al., 1994). Conversely, stem-girdling by threecornered alfalfa hoppers predisposes the same plants to the same diseases (Padgett et al., 1994; Hatcher et al., 1995). Thus, the role of insects in triggering resistance or susceptibility to both insects and phytopathogens is still under investigation.

It has recently been recognized that the oral secretions from some herbivores may trigger the release of plant volatiles that may attract the natural enemies of herbivores. For example, β-glucosidase in the regurgitant of *Pieris brassicae* caterpillars elicits the release of volatile compounds from cabbage leaves (Mattiacci et al., 1995; Proceedings of the National Academy of Science USA). More recently a glutamine-linolenic acid conjugate named volicitin was isolated from the regurgitant of beet armyworms *Spodoptera exigua* and found to induce the release of volatiles from corn seedlings (Alborn et al., 1997; Science).

Currently, Monsanto Company (700 Chesterfield Village Parkway, St. Louis, Mo. 63198) has expressed the gene encoding the fungal (*Asperhillils niger*) glucose oxidase in potatoes to confer disease resistance (Wu et al., 1997; Plant Physiol. 115:427–435). Monsanto postulated that active oxygen species perform multiple functions in plant disease, but their exact role in plant resistance to diseases is not fully understood. Monsanto demonstrated $H_2O_2$-mediated disease resistance in transgenic potato (*Solanum tuberosum*) plants expressing a foreign gene encoding glucose oxidase. In Monsanto's research, they provided evidence that the $H_2O_2$-mediated disease resistance in potatoes was effective against a broad range of plant pathogens. Monsanto also investigated the mechanisms underlying the $H_2O_2$-mediated disease resistance in transgenic potato plants. They report that the constitutively elevated levels of $H_2O_2$ induce the accumulation of total salicylic acid severalfold in the leaf tissue of transgenic plants, although no significant change was detected in the levels of free salicylic acid. The mRNAs of two defense-related genes encoding the anionic peroxidase and acidic chitinase were also induced.

In addition, an increased accumulation of several isoforms of extracellular peroxidase, including a newly induced one, was observed. This was accompanied by a significant increase in the lignin content of stem and root tissues of the transgenic plants. The results suggest that constitutively elevated sublethal levels of $H_2O_2$ are sufficient to activate an array of host defense mechanisms, and these defense mechanisms may be a contributing factor to the $H_2O_2$-mediated disease resistance in transgenic plants.

Monsanto conducted further research and reported that plant defense responses to pathogen infection involve the production of active oxygen species including hydrogen peroxide ($H_2O_2$). Monsanto obtained transgenic potato plants expressing a fungal gene encoding glucose oxidase, which generates $H_2O_2$ when glucose is oxidized. $H_2O_2$ levels were elevated in both leaf and tuber tissues of these plants.

The transgenic potato tubers exhibited strong resistance to a bacterial soft rot disease caused by *Erwinia carotovora* subsp. *carotovora* and disease resistance was sustained under both aerobic and anaerobic conditions of bacterial infection. This resistance to soft rot was apparently mediated by elevated levels of $H_2O_2$ because the resistance could be counteracted by exogenously added $H_2O_2$ degrading catalase.

The transgenic plants with increased levels of $H_2O_2$ also exhibited enhanced resistance to potato blight caused by *Phytophthora infestans*. The development of lesions resulting from infection by *P. infestans* was significantly delayed in leaves of these plants. Thus, the expression of active oxygen species-generating enzyme in transgenic plants represents a novel approach for engineering broad-spectrum disease resistance in plants.

The Salk Institute in La Jolla, Calif. has also used a similar approach to produce disease resistant rice. The Australian Science Foundation CSIRO scientists have also developed a disease resistant cotton using the same gene.

In addition to the use of glucose oxidase in crops for plant resistance, glucose oxidase has been applied to crops to inhibit foliar pathogens, as is discussed by D. R. Fravel, J. A. Lewis, and J. C. Chittams in "Alginate prill formulations of *Talaromyces flavus* with organic carriers for biocontrol of *Verticillium dahliae*," Phytopathology 85:165–168 (1985). U.S. Pat. No. 5,094,951, also discusses the production of glucose oxidase in recombinant systems.

While glucose oxidase may be used with various agricultural applications, it may also be used for other applications. For example, glucose oxidase has been used with various food applications. U.S. Pat. No. 5,085,873 shows a process for the treatment of a non-food product for assuring its microbial decontamination. U.S. Pat. No. 4,996,062 shows a glucose oxidase food treatment and storage method. U.S. Pat. No. 4,990,343 shows an enzyme product and method of improving the properties of dough and the quality of bread. U.S. Pat. No. 4,957,749 shows a process for removing oxygen in foodstuffs and in drinks. U.S. Pat. No. 4,929,451 shows a process for eliminating disagreeable odor from soya milk. U.S. Pat. No. 4,557,927 shows various food products and processes for producing the same. U.S. Pat. No. 3,804,715 shows a process for preparing sugar containing maltose of high purity. U.S. Pat. No. 3,767,531 shows a preparation of insolubilized enzymes and U.S. Pat. No. 4,675,191 shows a method for production of a low alcoholic wine.

Glucose oxidase may also be used for other applications including biomedical and biochemical. For example, glucose oxidase may be used in the glucose monitoring of blood, urine, etc. as discussed by J. A. Lott and K. Turner in "Evaluation of Trinder's glucose oxidase method for measuring glucose in serum and urine," Clin. Chem. 21 (12):1745–1760 (1975). Glucose oxidase may also be used in enzymatic test strips, such as the ones marketed by Lilly under the tradename TES-TAPE®, to detect glucose in urine. Yet another example is shown in U.S. Pat. No. 5,304,468, which shows areagent test strip and apparatus for determination of blood glucose.

Glucose oxidase may also have other medical uses, such as the development of anticancer and/or antitumor agents as reported by C. F. Nathan and Z. A. Cohn in "Antitumor Effects of Hydrogen Peroxide in Vivo," J. Exp. Med, Vol. 154, 1539–1553 (1981) and by Sanmoszuk M. D. Ehrlich and E. Ramzi in "Preclinical Safety Studies of Glucose Oxidase," J. Pharmacol. Exp. Ther. 266(3):1643–1648 (1993). Also, as reported by P. Heiss, S. Bernatz, G. Bruchelt and R. Senekowitsch-Schmidtke in "Cytotoxic Effect of Immunoconjugate Composed of Glucose Oxidase Coupled to a Chimeric Anti-ganglioside (GD2) Antibody on Spheroids," Anticancer Res. 15(6A):2438–2439 (1995). They report that the therapeutic use of the chimeric anti-ganglioside (GD2) antibody shows some success in the therapy of neuroblastomas and melanoma as shown in various Phase I studies. To enhance the effect, glucose oxidase is coupled to the anti-GD2 antibody to produce $H_2O_2$ in the presence of glucose and oxygen. $H_2O_2$ easily penetrates the target cells in contrast to the antibody.

Glucose oxidase may also be used for the production of antimicrobial products such as soaps and cremes; for example, Kitchen Cupboard Almond Milk Kitchenhand Creme 2 oz. contains glucose and glucose oxidase. Also, glucose oxidase may be used in synthetic saliva, such as Biotene and the like, since many saliva contain an optimum concentration of a natural enzyme system that regulates the microbiological oral ecosystem (glucose oxidase+ lactoperoxidase system).

Biochemical applications could also include Immunochemistry. Glucose oxidase may be used for immunohistochemistry, ELISA's and blot detection, such as in the antigen detection system marketed by Vector Laboratories under the tradename VECTASTAIN® ABC. It could also be used for identifying and/or tracking proteins as reported by J. J. Marchalonis in "Enzymatic Iodination of Proteins," Biochemical Journal, 113, 229–305, (1969) and by J. I. Thorell and B. G. Johansson, Biochemica et Biophysica Acta, 251,363–9, (1969).

Other uses could include enzymatically amplified sensors for amperometry and voltammetry including electrodes designed for amperometric detection of glucose. For example, enzyme reactions have been widely explored in combination with the electrode chemical techniques to add specificity to voltammetry and amperometry. Such strategies are often referred to as "biosensors" since they employ a biomolecule (e g. enzyme, antibody) and can be used for sensing purposes. The most common situation is to use an oxidase enzyme to detect its primary substructrate (e.g. glucose oxidase to detect glucose). The enzyme typically oxidizes the substrate and then transfers reducing equivalence (electrons) to a small molecule (acceptor or mediator) which can be oxidized at the electrode surface. Electrodes designed for the amperometric detection of glucose, lactate and cholesterol are common examples which have used this technique.

Research has been conducted to design various different types of enzyme electrodes. Using the analyte molecule functioning as a mediator, a saturating excess of the enzyme's substrate is used to make the reduced enzyme kenitically inexhaustible. Once an analyte molecule is oxidized at an electrode surface, it is rapidly reduced by the enzyme and is hence available for re-oxidation. This means that each analyte molecule is detected several times on the experimental time scale, thus, the analytical signal is chemically amplified by the enzyme reaction. For example, catechol analytes using glucose oxidase have been proposed.

Thus, a need exists to continue investigating the interaction of insects with plants to explore methods for improving agriculture. There is also a continuing demand for alternative sources of glucose oxidase for various fields including biomedical, biochemical, food production and preservation, and the like.

SUMMARY OF THE INVENTION,

The present invention addresses the above-referenced needs in the art. The present invention involves the characterization of the major salivary enzyme of the corn earworm *Helicoverpa zea*. The enzyme's role in triggering resistance to bacterial blight *Pseudomonas syringae* pv. *glycineae* and frogeye leafspot *Cercospora sojina* in soybeans and its role in triggering resistance to insects in tomatoes are also involved in the present invention.

The invention includes an enzyme or a novel protein. The enzyme is secreted from the salivary glands of certain insects. We have found glucose oxidase activities in the saliva of species belonging to the order Hymenoptera and Lepidoptera. In particular, the regurgitant of *Helocoverpa zea* obtained from the functional salivary glands (i. c. labial and submandibular) was purified by isoelectric focusing to obtain an enzyme with high glucose oxidase activity.

The *H. zea* enzyme is a protein that possesses glucose oxidase activity. The amino acid sequence of the protein is unique, sharing less than 25% humology with other reported protein structures. In particular, the novel protein structure shares very little homology with other proteins known to have the similar function of glucose oxidation.

When the *H. zea* protein is applied to plants, it triggers disease and insect resistance systematically through the plant. For example, the protein triggers resistance in plants when applied at quantities as small as 10 $\mu$g. The enzyme was tested on soybean plants to protect them from bacterial blight and frogeye leaf spot. The treatment was also applied to tomato plants to reduce and/or control larval infestations.

It is anticipated that, at least a partial sequence of the protein can be cloned and sequenced, and can be expressed in plants to develop transgenic plants that possess broad spectrum resistance. The physical and kinetic attributes of the *H. zea* glucose oxidase enzyme are a pH of 7.0, a pI of 4.4 and a molecular weight of 88 kd. The $k_m$ and $V_{max}$ of the enzyme for glucose is 26.9 mmol and 26.7 $\mu$mol $min^{-1}$ $mg^{-1}$, respectively.

Since the enzyme is specific for glucose, it may also be used for the chemical monitoring of glucose for a wide variety of purposes, including biomedical, biochemical, etc. Since the enzyme scavenges oxygen and produces hydrogen peroxide, it may also be used in food products for protection of food quality. The production of hydrogen peroxide also suggests the use of the protein as an antimicrobial agent in food preservation.

The potential applications for the present enzyme with glucose oxidase activity are widely varied. They include many agricultural uses including the expression in crops for plant resistance and the application to crops for inhibiting foliar pathogens and/or other pests. The enzyme may be used in food applications for improving the shelf life or quality of the food products as well as the production of low alcohol products. Biomedical uses include using the enzyme for glucose monitoring of blood, urine, etc, as well as using the enzyme in the development of anti-cancer and/or anti-tumor agents. The enzyme may also be utilized in the production of antimicrobial products and the like. Various biochemical applications include the use of the enzyme in immunochemistry as well as for the enzymatic iodination of proteins and enzymatically amplified sensors for amperometry and voltammetry. Another possible use of the gene from the enzyme is an expression in a Baculovirus for pesticide usage.

Thus, a principal object of the present invention is the provision of an insect salivary enzyme.

Another object of the present invention is the provision of an insect salivary enzyme which triggers systemic resistance in plants.

Still another object of the invention is to provide an enzyme that may be used to improve agricultural practices.

Another object of the present invention is to provide an enzyme that may be expressed in plants to improve their disease resistance.

Another object of the present invention is to provide an enzyme or protein with glucose oxidase activity that may be used in a wide variety of applications.

A related object of the present invention is to provide an enzyme that may be used for food preservation and/or food protection.

Another basic object of the present invention is to provide an enzyme isolated from the saliva of an insect with saliva having a high concentration of proteins with glucose oxidase activity.

Another object of the present invention is to provide a protein that may be expressed in soybean plants to improve their resistance to various diseases.

Another object of the present invention is to provide an enzyme that reduces the susceptibility of soybean and/or tomato plants to undesirable pests.

Yet another object of the present invention is to provide an enzyme with glucose oxidase activity that may be used in the biomedical, biochemistry, amperometry and voltammetry applications.

Another object of the present invention is to provide an enzyme that may be incorporated into agricultural chemicals to confer desirable benefits to plants.

Another object of the present invention is to provide an enzyme with a high glucose oxidase activity that may be harvested from insects.

Other objects and further scope of the application of the present invention will become apparent from the detailed description to follow, taken in conjunction with the accompanying drawings.

BRIEF DESCRIPTION OF THE DRAWINGS

FIG. 1 is a graph depicting the percent of infection versus time for a control group and an insect group;

FIG. 5 is a table depicting the source of salivary hydrogen peroxide;

FIG. 15 is a graph depicting the systemic resistance to *Cercospora sojina* with the percent of infection versus days post-infection for a water group and an insect GOX group;

FIG. 16 is a graph depicting the systemic resistance to *Pseudomonas syringae glycinea* with percent infection versus days post infection for a control group and insect GOX group;

FIG. 17 is a bar graph depicting the systemic resistance to *H. zea* in tomato leaves with percent survival for a control treatment, water treatment and insect GOX treatment, and, FIG. 18 is a bar graph depicting the systemic resistance to *H. zea* in leaves with larval weight for a control treatment, water treatment and insect GOX treatment.

DETAILED DESCRIPTION OF THE PREFERRED EMBODIMENTS

In the study of the present invention, it was observed that insect feeding triggers systemic acquired resistance against *Cercospora sojina* (FIG. 1) in some plants. Species belonging to the orders Hymenoptera and Lepidoptera often have saliva that has elevated glucose oxidase activity. For example, many species of the superfamily Noctuiodea including *H. zea* have especially elevated levels of glucose oxidase activity. The honey bee of the species *Apis mellifera* of the Hymenopteran order also has elevated levels of glucose oxidase activity. Other examples of species exhibiting elevated levels of glucose oxidase activity in their saliva include *Heliothis virescens, Heliothis subflexa, Spodoptera frugiperda, Trichoplusia ni, Manduca sexta,* and *Apis mellifera.*

Figure 2:
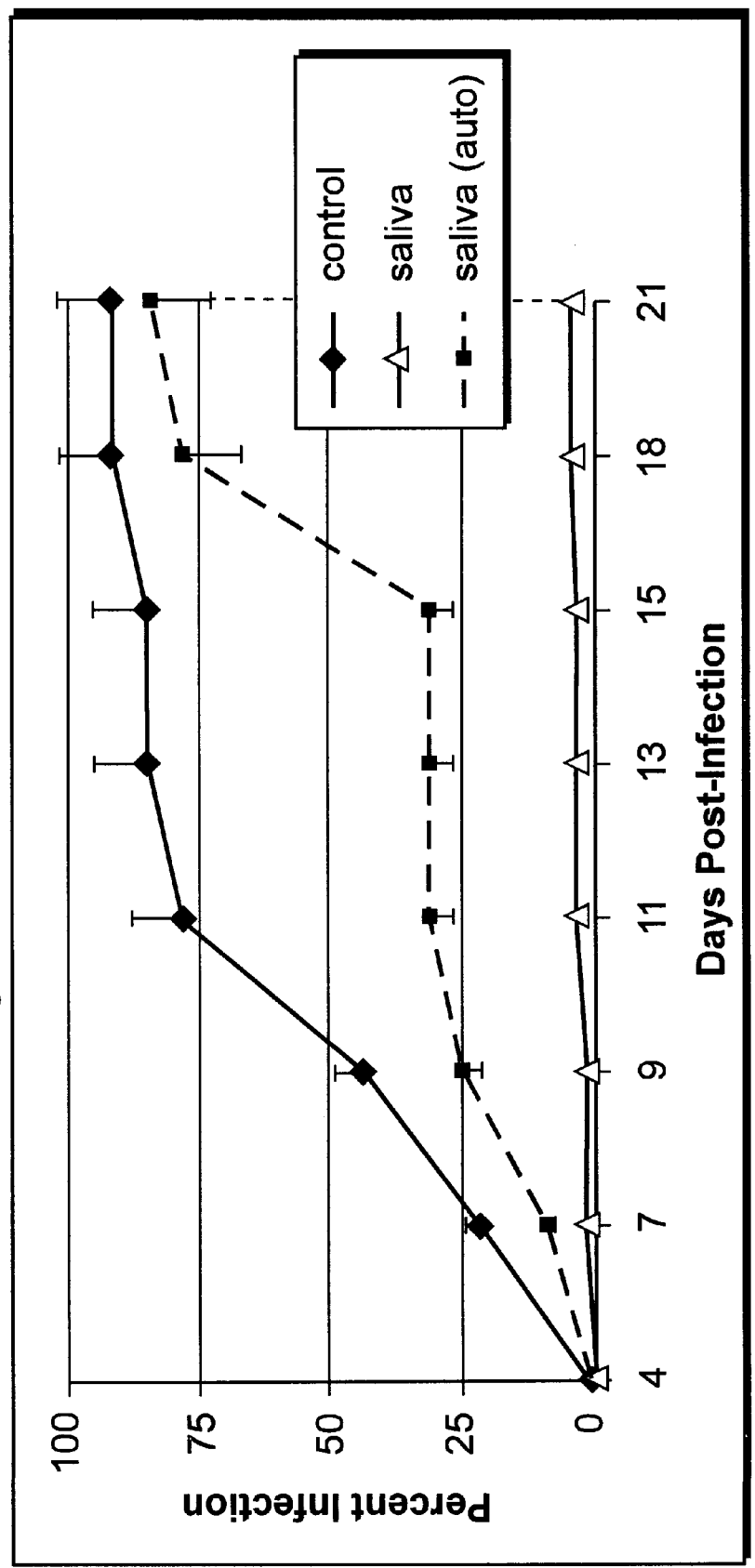
FIG. 2 is a graph depicting the percent infection versus the time for a control group, a saliva group and another saliva group.
Figure 3:
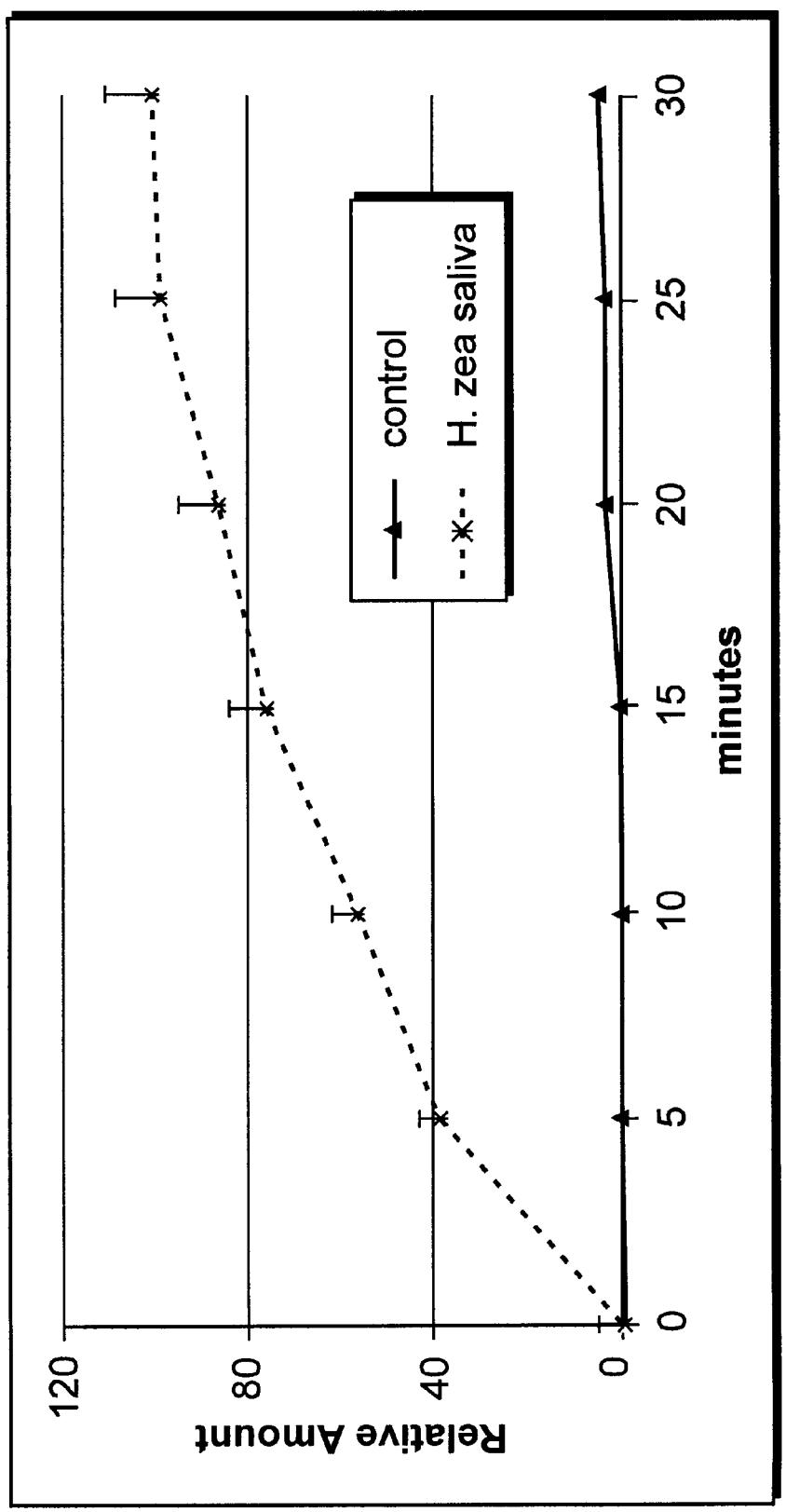
FIG. 3 is a graph depicting the relative amount of hydrogen peroxide formation in soybean cell cultures versus time for a control group and *H. zea* group.
Figure 4:
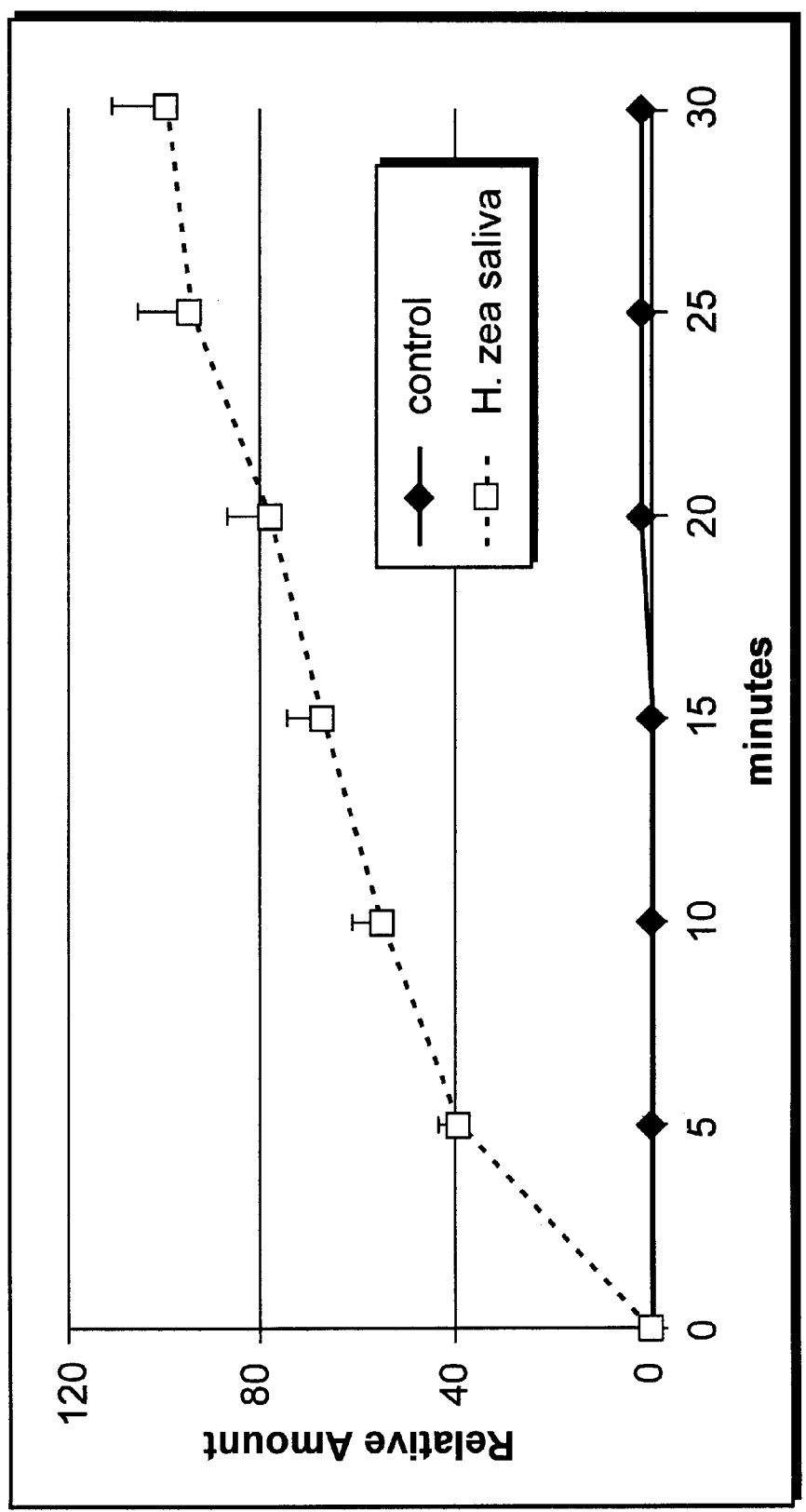
FIG. 4 is a graph depicting the relative amount of peroxide formation in plant cell media versus time for a control group and a *H. zea* saliva group.

In particular, predation by the corn earworm *Helicoverpa zea* appears to activate the defense mechanisms of several plants, including soybeans and tomatoes. Further observation has identified the saliva of *H. zea* as the mechanism for triggering these defenses (FIG. 2). Further investigation of this phenomena has revealed that the saliva triggers hydrogen peroxide formation in the plants (FIGS. 3–4).

The saliva of *H. zea* appears to be absorbed by the plant and causes the subsequent production of hydrogen peroxide.

Figure 6:
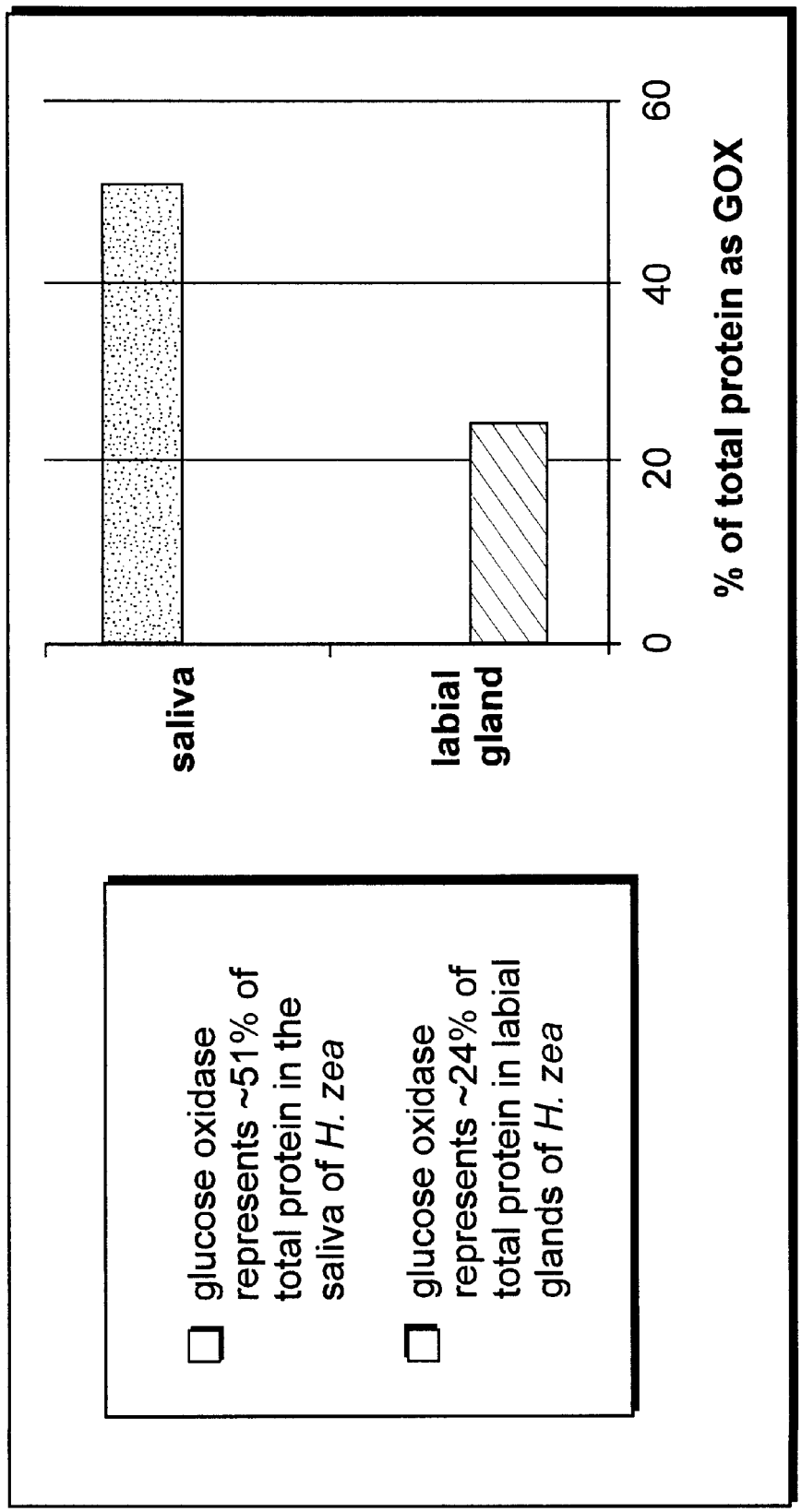
FIG. 6 is a bar graph depicting the concentration of glucose oxidase in *H. zea* saliva and labial glands.
Figure 7:
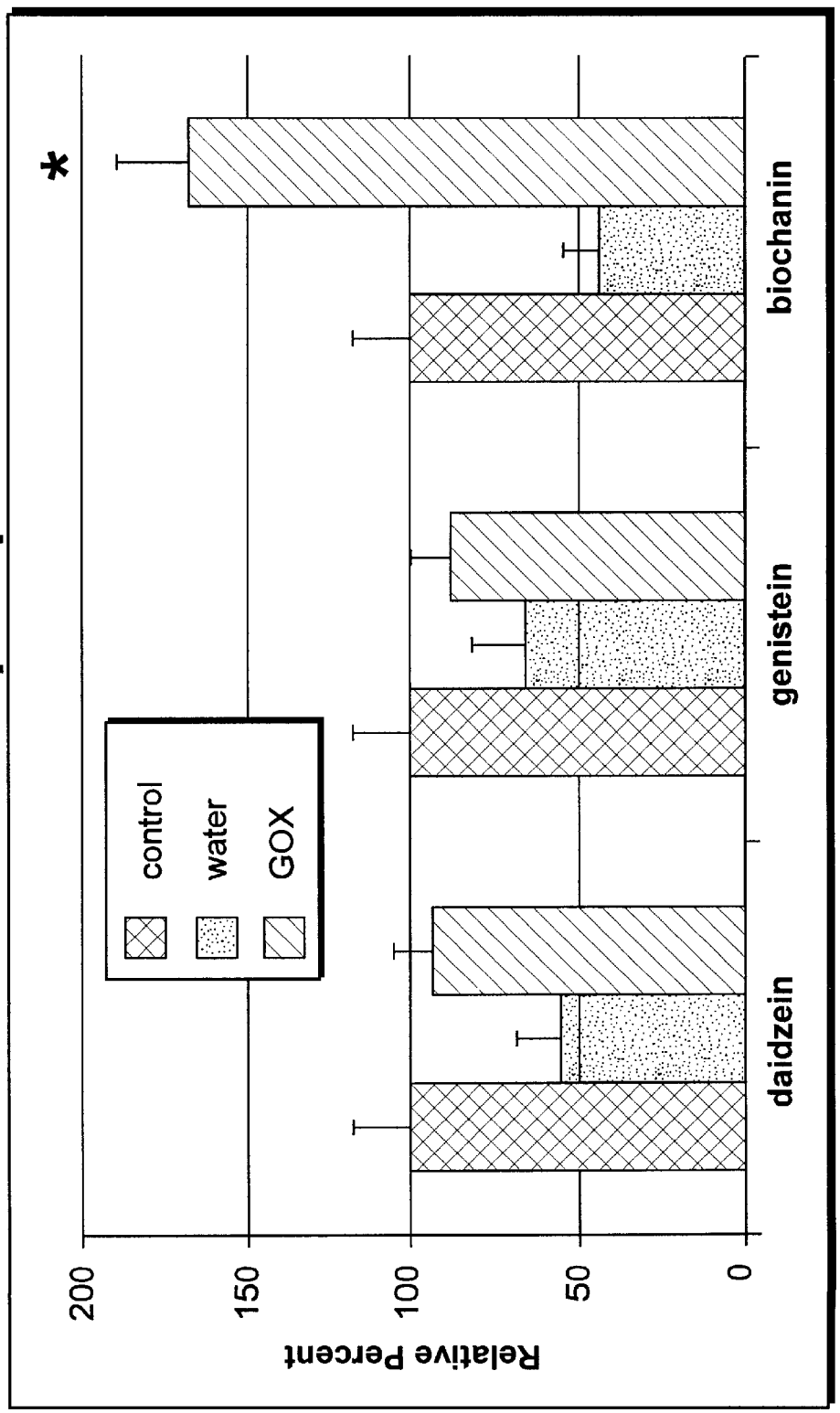
FIG. 7 is a bar graph representing the localized effect of salivary glucose oxidase on relative percent of the phytoalexins daidzein, genistein and biochanin respectively; for a control treatment, water treatment and GOX treatment.
Figure 8:
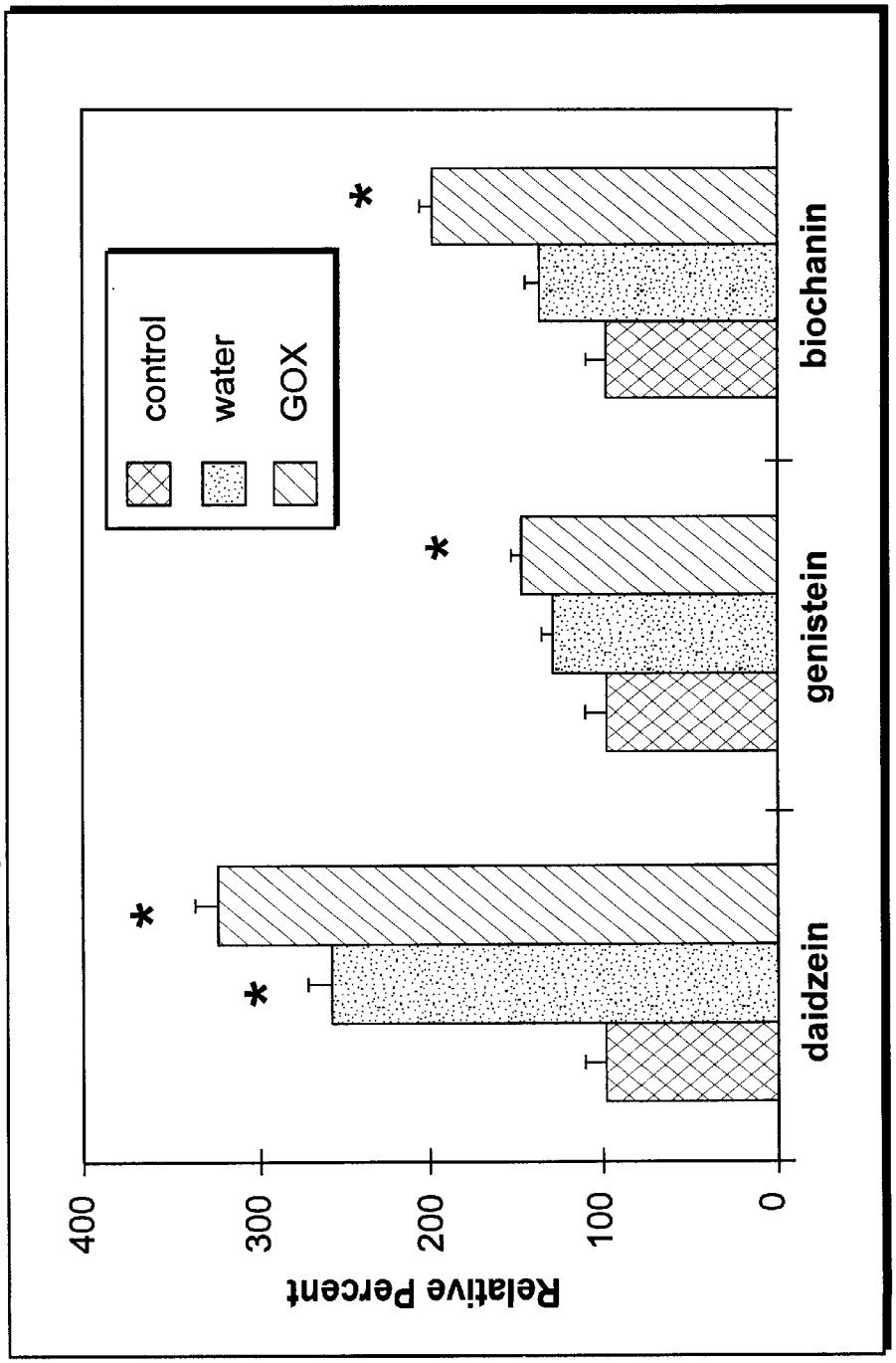
FIG. 8 is a bar graph showing the systematic effect of salivary glucose oxidase on the relative percent of the phytoalexins daidzein, genistein and biochanin respectively for a control treatment, water treatment and GOX treatment.
Figure 9:
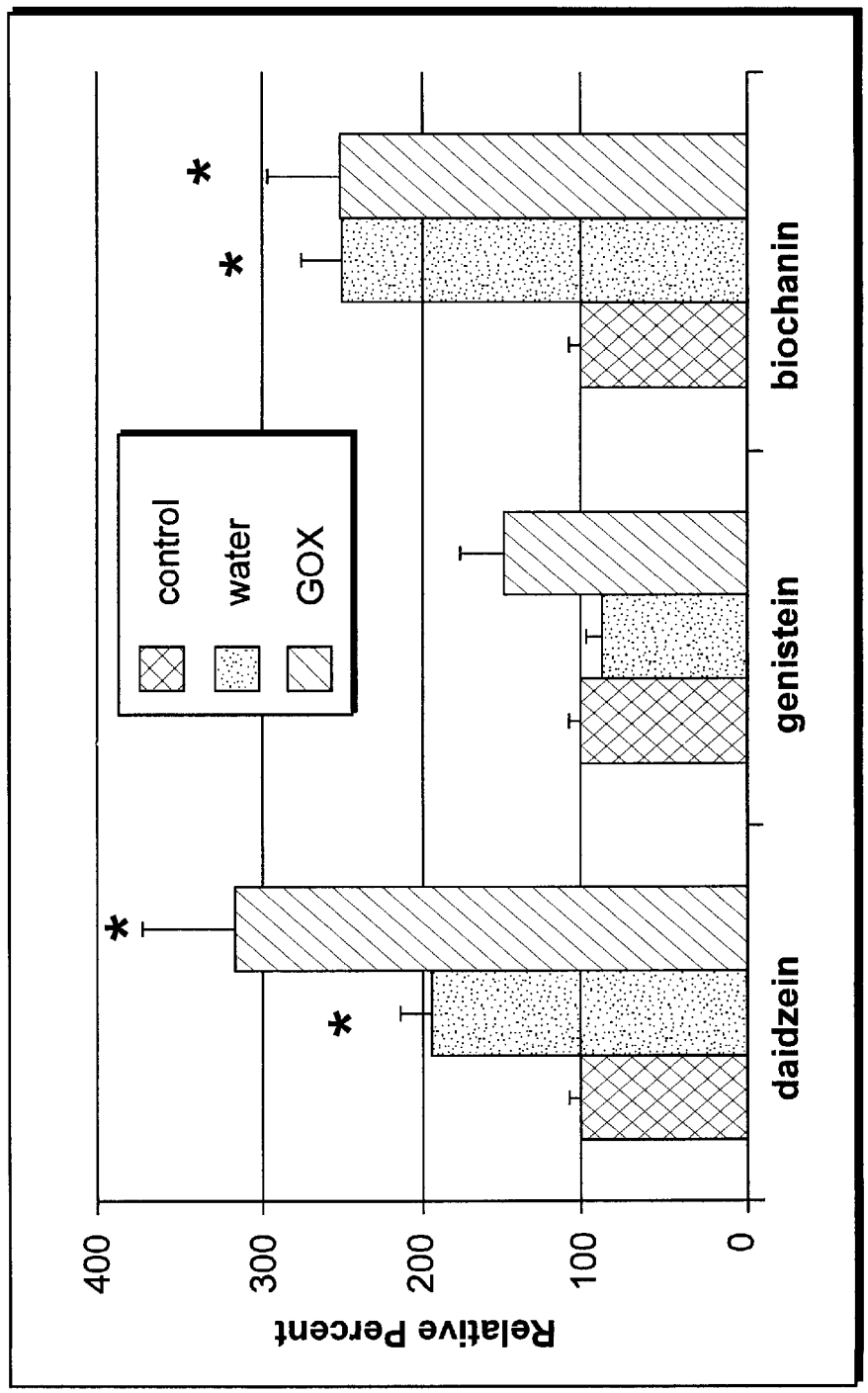
FIG. 9 is a bar graph depicting the systemic effect of salivary glucose oxidase on the relative percent of the phytoalexins daidzein, genistein and biochanin respectively for a control treatment, water treatment and GOX treatment.
Figure 10:
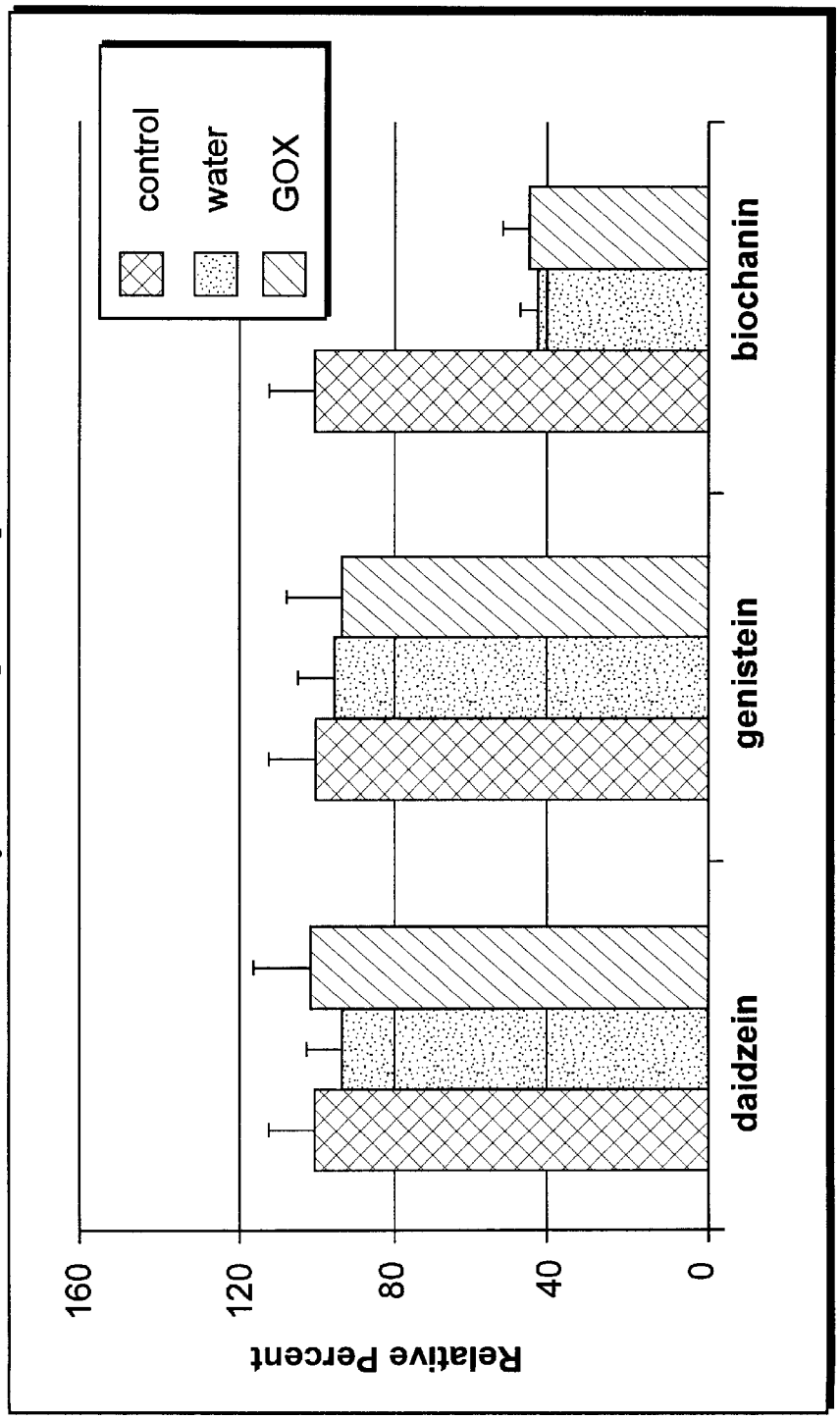
FIG. 10 is a bar graph depicting the systemic effect of salivary glucose oxidase on the relative percent of the phytoalexins daidzein, genistein and biochanin respectively for a control treatment, water treatment and GOX treatment.
Figure 11:
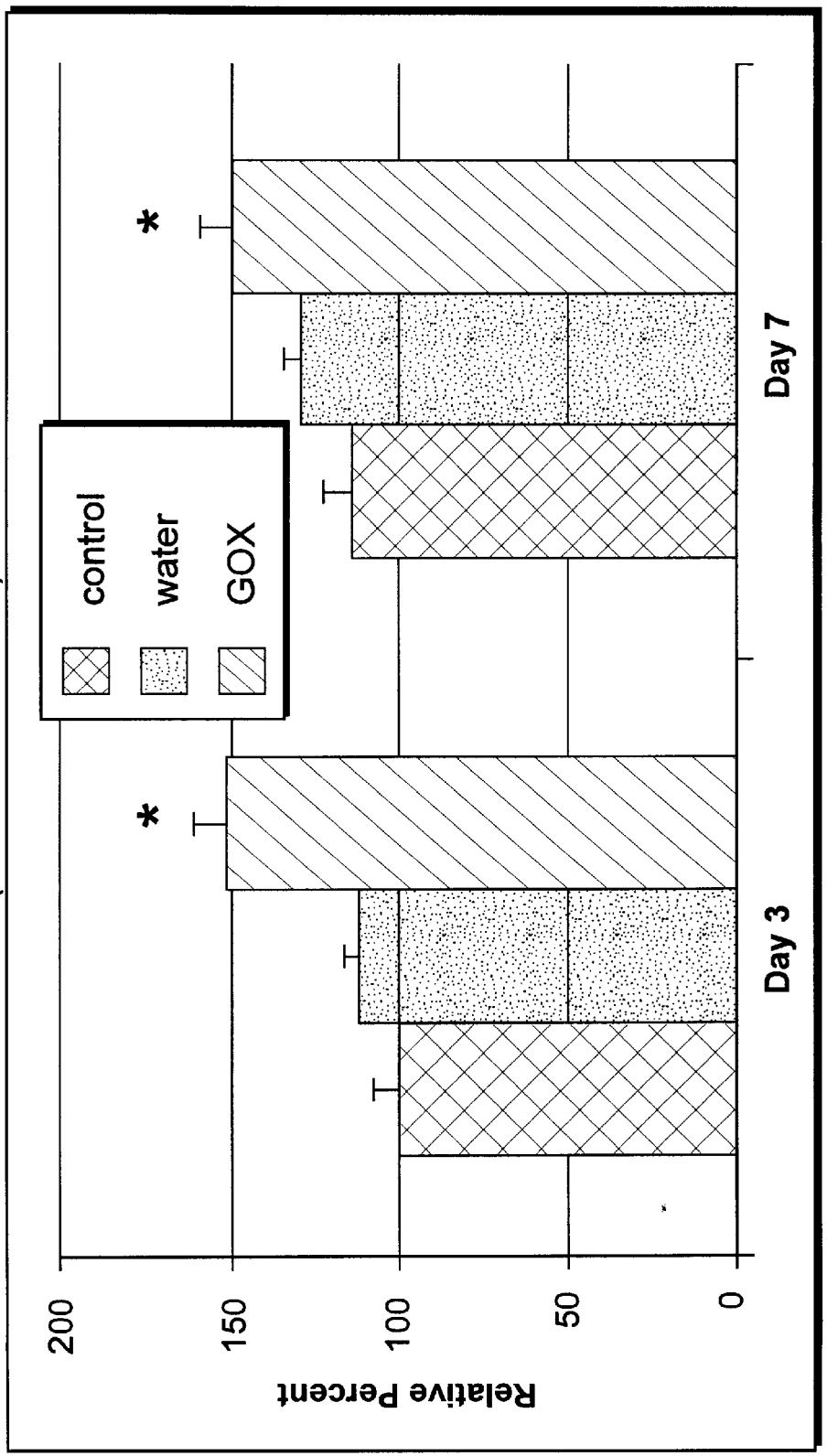
FIG. 11 is a bar graph depicting the localized effect of salivary glucose oxidase on the relative percent of salicylic acid at day 3 and day 7 respectively for a control treatment, a water treatment and GOX treatment.
Figure 12:
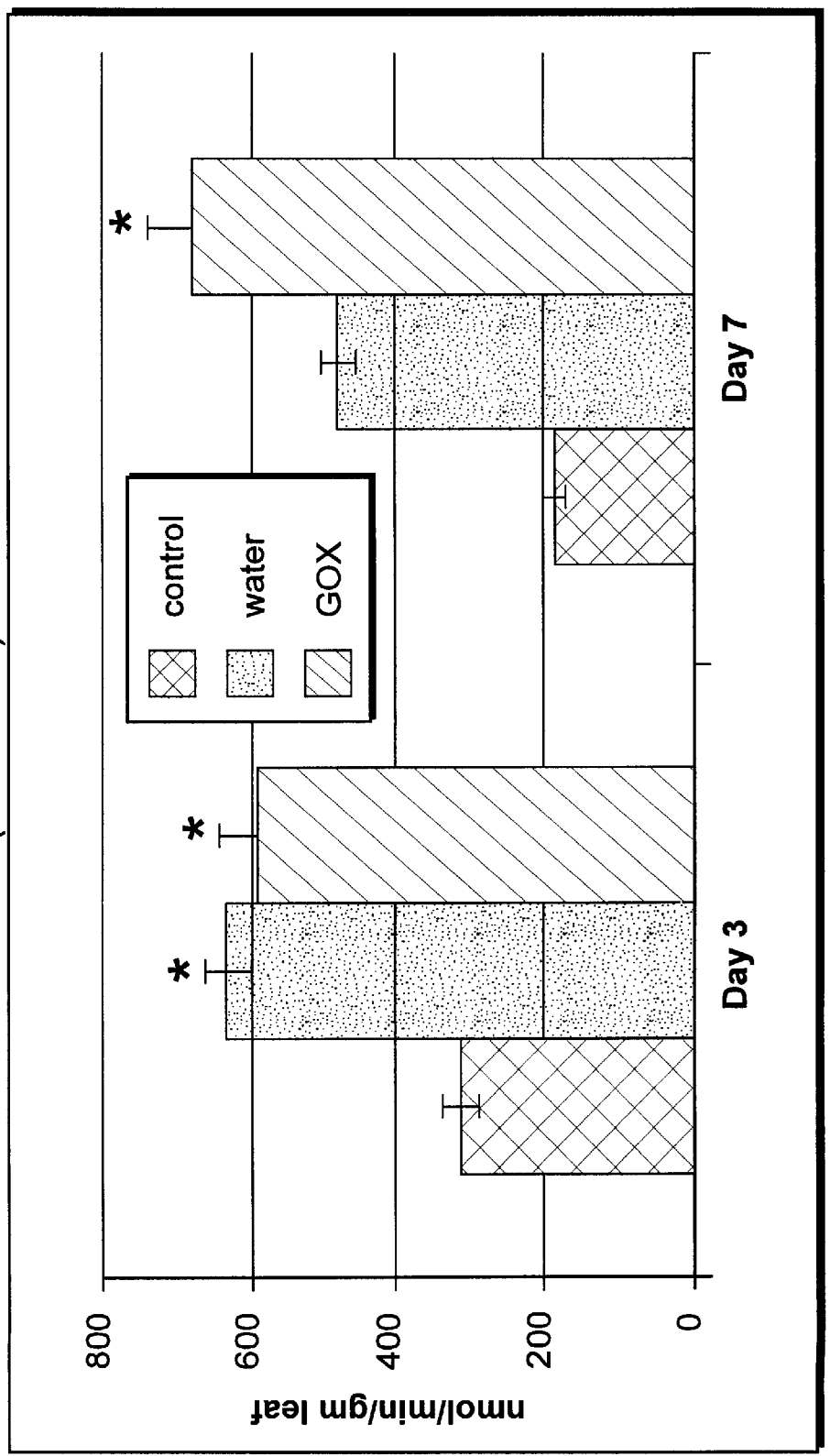
FIG. 12 is a bar graph depicting the localized effect of salivary glucose oxidase on the concentration of lipoxygenase at day 3 and day 7 respectively for a control treatment, a water treatment and GOX treatment.
Figure 13:
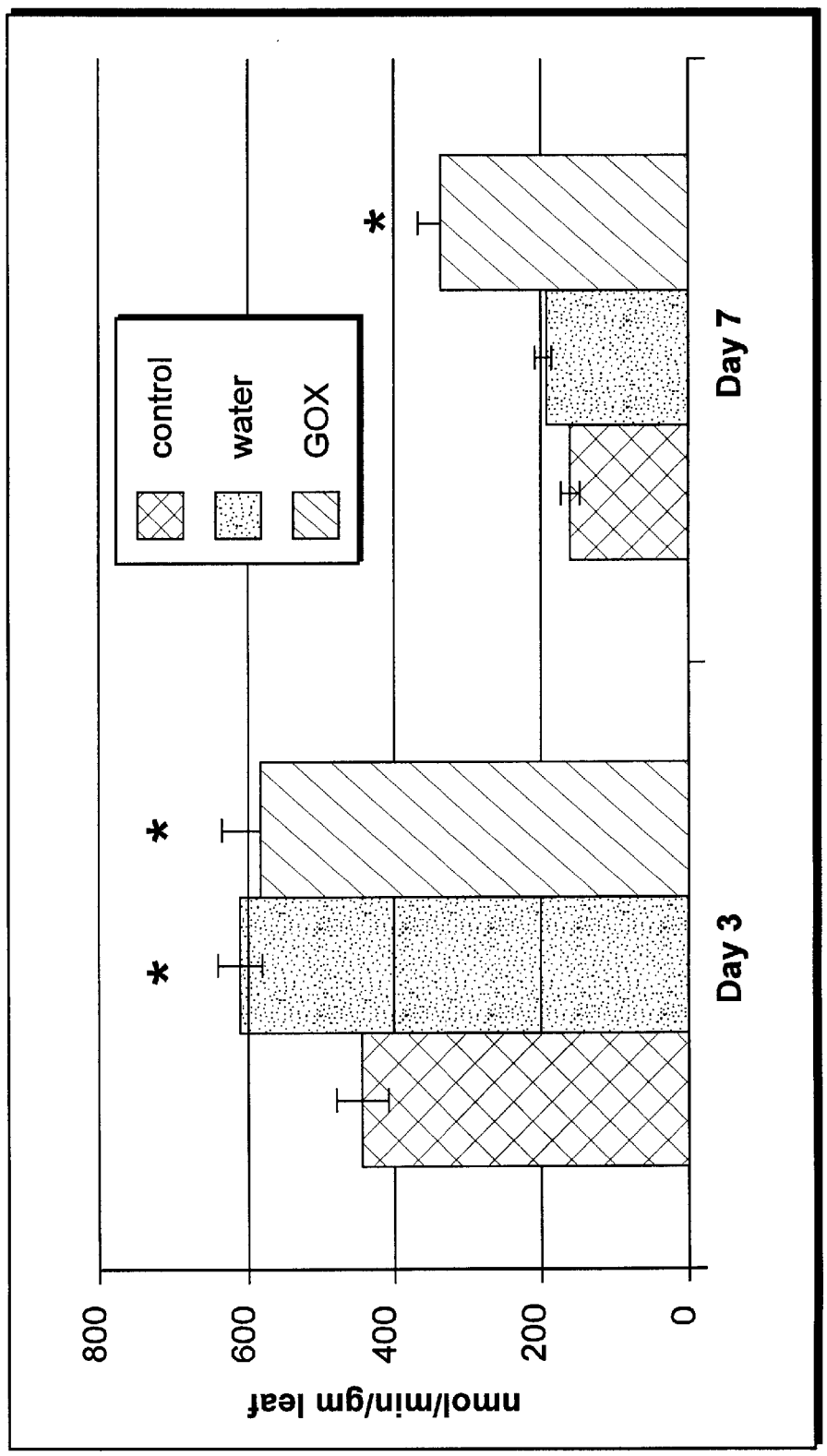
FIG. 13 is a bar graph depicting the systemic effect of salivary glucose oxidase on the concentration of lipoxygenase at day 3 and day 7 respectively for a control treatment, a water treatment and a GOX treatment.

The source of this salivary hydrogen peroxide was further identified as a protein or enzyme, more particularly, glucose oxidase (GOX) as is shown in FIGS. 5 and 6. The insect salivary glucose oxidase had several affects upon the plants in addition to the increased production of hydrogen peroxide. For example, the salivary GOX resulted in an increase in pyotoalexins locally and systemically throughout the plant for an extended period of time (FIGS. 7–10). The salivary GOX also resulted in increased levels of salicylic acid locally, but not systemically (FIG. 11). The salivary GOX also increased lipoxyenase activity both locally and systemically (FIGS. 12–13). Consequently, the enzyme was isolated and purified to be studied more closely.

The enzyme with glucose oxidase (GOX) activity was found in great abundance in the functional salivary glands of *H. zea*. Labial and submandibular gland extracts were produced by dissecting the glands from actively feeding, 6th instar *H. zea*. The dissected glands were homogenized with a hand-held pestle in a microcentrifuge tube. The resulting homogenate was then centrifuged to obtain supernatant.

The supernatant from extracts of approximately 350 parts of labial glands was concentrated in 10,000 MWCO Centriplus concentrators (Amicon) until the sample volume was less than 2.0 ml. The sample was prepared for isoelecric focusing (IEF) by bringing the volume of the sample to 50 ml with 3.0 M urea, 1 mM PMSF. biolyte ampholytes (Bio-Rad, Richmond, Calif.), 2.0 ml of pH 3–9 ampholytes, were added to the sample and the mixture was loaded onto a Bio-Rad otofor for IEF (VXH=3500). (Met Ile Leu Ala Gln Gln Asp Xaa Gly Xaa Gln Thr Val Val Glu Gly Ala Ser Ile Leu Asn Ser Xaa Thr Ala Xaa Val Xaa Thr Tyr)(met ile leu ala gjn gln asp $X_{aa}$ gly $X_{aa}$ gln thr val val glu gly ala ser ile leu asn ser $X_{aa}$ thr ala $X_{aa}$ val $X_{aa}$ thr tyr)

Fractions from the IEF with glucose oxidase activity were then combined, the volume of the combined fractions was brought to 18 ml with the urea solution, and IEF was repeated on the Mini-Rotofor (Bio-Rad) (VXH=8000).

The 20 fractions from the second IEF were then assayed for GOX activity and total protein. The fractions with GOX activity were then run on SDS-PAGE to asses purity. The protein with GOX activity from the labial glands of actively feeding *H. zea* resulted in an enzyme preparation that was purified 23× (Table 1).

TABLE 1

Purification of GOX Enzyme from actively feeding, 6th instar *H. zea*

| Purification Step | % Recovery | Purification | Activity[1] |
|---|---|---|---|
| Homogenate | 100.0 | — | 1,223.9 |
| Concentrate | 68.6 | 0.74X | 911.0 |
| Rotofor | 4.04 | 7.36X | 9,083.0 |
| Mini-Rotofor | 0.33 | 23.10X | 28,174.1 |

[1]Activity is expressed in nmol min$^{-1}$ mg$^{-1}$

The GOX activity of Table 1 was determined by measuring the change in absorbance of a reaction mix at 436 nm. Calculations of activity were made using an extinction coefficient of 8.3 cm$^{-1}$ $\mu$M$^{-1}$ (Methods of enzymatic analysis). The reaction mixture contained 0.17 mM o-dianisidine in 0.1 M potassium phosphate (7.0), 92.7 mM D-glucose. 10 $\mu$l of 2.0 mg/ml peroxidase and 10 $\mu$l of the sample were added to reach a total volume of 1.52 ml.

The effect of "Inhibitors" on GOX activity was also measured. Five different substances (o-phthalate, silver chloride, p-chloromercuribenzenesulfonic acid (PCMS), 2-deoxy-D-glucose, and L-glucose) were tested for inhibitory effects on the GOX activity. Each substance was mixed with an aliquot of the *H. zea* extract at 5.0 mM and allowed to incubate for 15 min at 4° C. The samples were then checked for GOX activity.

The substrate utilization of GOX was also measured. Fifteen sugars (D-glucose, L-glucose, 6-deoxy-D-glucose, 2-deoxy-D-glucose, L-sorbose, D-xylose, D-galactose, sucrose, cellobiose, trehalose, β-D-gluconolactone, 2-deoxy-D-ribose, rhamnose, fucose, and arabinose) were tested for activity with the *H. zea* GOX. All substances were tested at an equal concentration of 92.7 mM, replacing glucose, in the GOX assay. Pectin was also tested for utilization by glucose oxidase at 10 mg/ml.

*H. zea* GOX was fairly specific for the sugars that it was capable of utilizing; the enzyme had appreciable activity with only three of the twelve sugars tested. The GOX had highest activity with 6-deoxy-D-glucose, D-glucose, and xylose. The *H. zea* GOX also had some activity with xylose and pectin. The results are shown in Table 2.

TABLE 2

Substrates for GOX from *H. zea*.

| Substrate | Activity[1] | ± SE | Rel activity (%) |
|---|---|---|---|
| D-Glucose | 2428 | 306.3 | 100 |
| 6-Deoxy-D-Glucose | 2788 | 158.7 | 115 |
| Xylose | 1029 | 52.1 | 42.4 |
| Pectin | 73.4 | 63.5 | 3.02 |
| Sorbose | 40.0 | 18.0 | 1.65 |
| 2-Deoxy-D-Glucose | 32.3 | 25.4 | 1.33 |
| Cellobiose | 31.7 | 11.7 | 1.31 |
| Fucose | 30.6 | 20.7 | 1.26 |
| Sucrose | 9.0 | 7.9 | 0.37 |
| Gluconolactone | 7.1 | 6.0 | 0.29 |
| Trehalose | 5.1 | 3.3 | 0.21 |
| 2-Deoxy-D-Ribose | 3.6 | 2.8 | 0.15 |
| Rhamnose | 0.97 | 0.9 | 0.04 |
| Arabinose | 0.0 | 0.0 | 0.00 |
| L-Glucose | 0.0 | 0.0 | 0.00 |
| Galactose | 0.0 | 0.0 | 0.000 |

[1]Activity is expressed in nmol min$^{-1}$ mg$^{-1}$

Physical and kinetic attributes of the *H. zea* GOX were also determined. A pH optimum of 7.0 and a pI of 4.4, estimated by isoelectric focusing, were determined. A molecular weight of 88 kd was determined by SDS-PAGE analysis. Kinetic information was determined by testing the activity of the *H. zea* GOX with increasing concentrations of glucose, from 1.0 to 150.0 mmol, the $k_m$ and $V_{max}$ values were calculated using the HYPER program (v 1.p1, J. J. Easterby) by hyperbolic regression analysis and the $k_m$ and $V_{max}$ of the enzyme for glucose is 26.9 mmol and 26.7 $\mu$mol min$^{-1}$ mg$^{-1}$, respectively.

In these embodiments, the HYPER computer program was utilized to determine the $V_{max}$, the maximum velocity of the catalyzed reaction, and the $k_m$, the Michealis-Menton constant, for this enzyme. However, those skilled in the art will appreciate that for several years there have been a wide variety of methods used to calculate these two constants. Michaelis-Menten kinetics have been used for several decades by researchers to characterize enzymes. While there are differences in methods of attaining these constants, they generally produce no significant deviations in the values calculated. Those skilled in the art will appreciate that the method used to calculate these constants will depend on a variety of factors, including the enzyme studied, the substrate and the method of monitoring the reaction.

Figure 14:
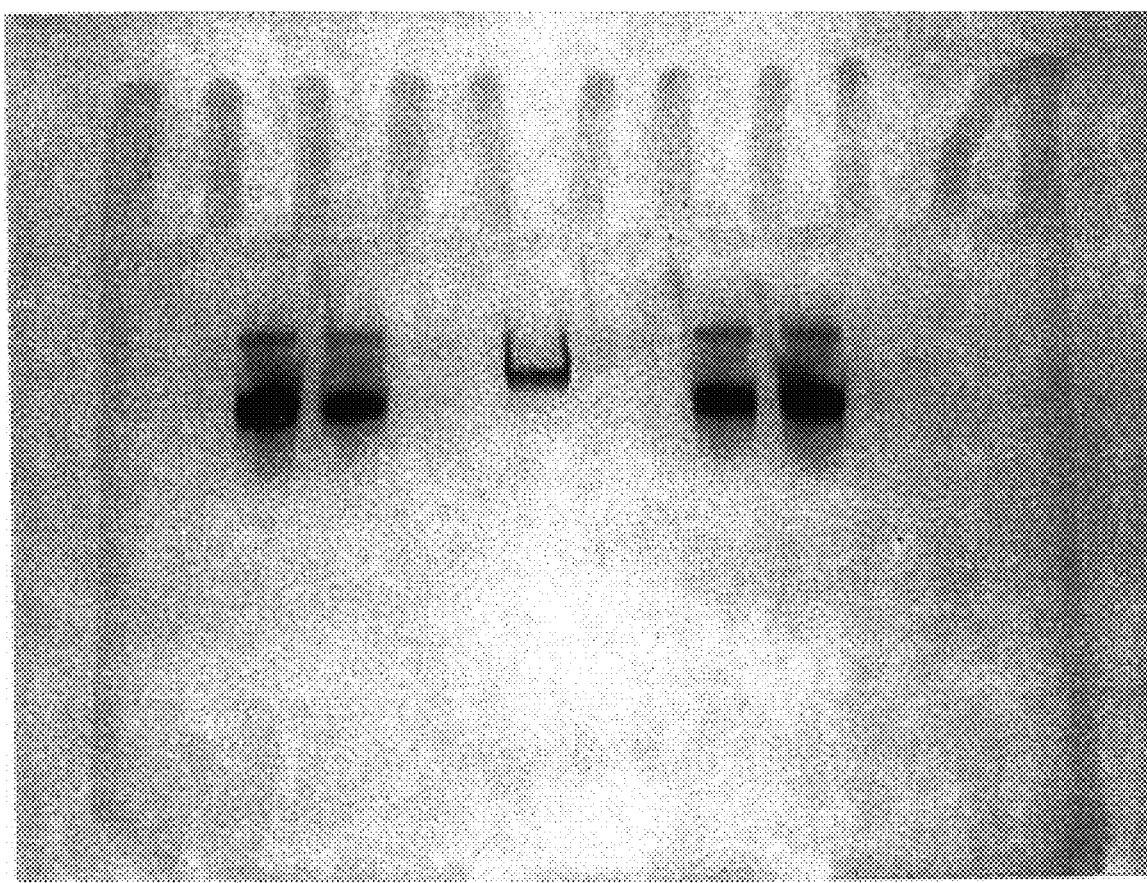
FIG. 14 is a reproduction of a photograph of a native polyacrylamide gel that was stained for GOX activity overnight in the same solution that is used for the GOX assay (including glucose, o-dianisdine, and peroxidase) with both fungal GOX and GOX isolated from *H. zea*. with lanes 2, 3, 7, and 8 containing the fungal GOX and lane 5 containing partially purified *H. zea* GOX.

The partially purified enzyme, 20 μg, was loaded onto two lanes of a 4–20% gradient pre-cast tris-glycine gel (Bio-Rad) and run under SDS-PAGE standard conditions (FIG. 14). The resulting gel was blotted onto an Immobilon-P (Millipore, Bedford, Me.) PVDF membrane using the Mini Trans-Blot Electrophoretic Transfer Cell (Bio-Rad). The PVDF membrane was stained with Coomassie blue following standard protocols and rinsed in distilled water. The *H. zea* GOX bands were excised from the membrane and sent to Commonwealth Biotechnologies, Inc. (Richmond, Va.) and to the Iowa State University Protein Facility for N-terminal sequencing.

The first 30 amino acids so the *H. zea* GOX were sequenced (SEQ ID NO: 1); unfortunately, all of the amino acids in the sequence could not be unambiguously assigned. The first 30 residues sequenced were as follows (with X's standing for unassignable residues): MILAQQDXGX-QTVVEGASILNSXTAXVXTY (SEQ ID NO 1).

The sequence was examined by predictive algorithms for secondary structure and immunogenic probability. A Ser residue was substituted for each X residue, and the entire sequence was analyzed according to the Kyte Doolittle and Chou Fasman algorithms. This segment of the protein is not predicted to conform to β-turn structure of a peptide immunogen. It is predicted to be helical in structure, or perhaps a helix leading to a β-strand C-terminal segment.

The sequence was used to search the Swiss Protein Data base, and did not show good homology with any listed sequence. Note also that the homologies found were not at the N-terminus of the proteins.

The effect of the *H. zea* salivary enzyme with GOX activity on the severity of bacterial blight and frogeye leaf spot in soybeans was tested in Example 1 and the effect on larval infestation in tomatoes was tested in Example 2 (FIGS. 15–18).

EXAMPLE 1

Four 0.5 cm disks were removed from each trifoliate leaf with a cork borer on the second node of a V3 stage soybean. The cultivar 'Williams' was used throughout the study. A total of ten micrograms of purified *H. zea* GOX was applied to each plant with a camel hair brush. Other treatments consisted of plants treated only with water and control plants that were left unwounded without leaf disk removal.

Three days following the removal of leaf disk and application of glucose oxidase, plants were inoculated with the respective pathogens using standard conditions and techniques. Disease severity was scored visually using standard disease rating scales for leaf pathogens during at three week period. The experiment was replicated four times using six plants per replicate for each treatment.

Treatment of soybean plants with *H. zea* GOX provided strong protection from the diseases bacterial blight and frogeye leaf spot (Table 3). Disease severity in the GOX treatment was significantly less than the control or water treatments throughout a three week period during which disease severity was monitored (FIGS. 15–16).

TABLE 3

Effect of Glucose Oxidase on Severity of Bacterial Blight and Frogeye Leaf Spot

| Treatment | % Infection Bacterial Blight | % Infection Frogeye Leaf Spot |
| --- | --- | --- |
| Control | 63.9 (7.8) | 81 (13.5) |
| Water | 54.6 (11.1) | 79 (9.8) |
| Glucose Oxidase | 9.1 (6.6) | 7.7 (5.3) |

EXAMPLE 2

Four 0.5 cm. disks were removed from each leaf with a cork borer on the second node of a four node tomato plant (cv. Mountain Pride). A total of ten micrograms of purified *H. zea* GOX was applied to each plant with a camel hair brush. Other treatments consisted of plants treated only with water and control plants that were left unwounded without leaf disk removal.

Three days following treatment, the terminal leaf was excised with a razor blade and placed in a clear plastic 250 ml container. Twenty neonate *H. zea* larvae were placed in each container. Larval survival and weights were recorded after five days. The experiment was replicated with 10 plants per treatment.

The treatment of tomato plants with *H. zea* GOX resulted in systemic resistance to *H. zea* larvae (Table 4). Larvae placed on foliage from GOX-treated plants displayed reduced survival and weight gain compared to larvae on control or water-treated plants (FIGS. 17–18).

TABLE 4

Effect of Glucose Oxidase on Insect Resistance in Tomato

| Treatment | % Larval Survival | Larval Weight (mg.) |
| --- | --- | --- |
| Control | 56.7 (7.0) | 3.0 (0.5) |
| Water | 37.5 (4.0) | 2.0 (0.5) |
| Glucose Oxidase | 28.0 (2.5) | 0.6 (0.6) |

The isolated and characterized novel protein from the saliva of an insect *Helicoverpa zea* possesses glucose oxidase activity and has specificity for glucose as a substrate. The amino acid sequence of this protein is unique and bears very little homology with published sequences of other glucose oxidase reported from fungi. The enzyme when applied to foliage triggers strong systemic resistance to a fungal and bacterial pathogen. For example, direct treatment of cultures of these pathogens with the glucose oxidase results in strong inhibition of their growth.

*H. zea* GOX was fairly specific for the sugars that it was capable of utilizing; the enzyme had appreciable activity with only three of the twelve sugars tested. The GOX had highest activity with 6-deoxy-D-glucose, D-glucose, and xylose (Table 2). The *H. zea* GOX also had some activity with pectin.

Whereas, the present invention has been described in relation to the above examples and drawings attached hereto, it should be understood that other and further modifications, apart from those shown or suggested herein, maybe made within the spirit and scope of this invention.

What is claimed is:

1. A glucose oxidase salivary enzyme isolated and purified from Helicoverpa having the following physiochemical properties:
   action: catalyzing the following reaction:
   glucose+$O_2$→gluconic acid+hydrogen peroxide
   optimum pH: approximately 7.0
   isoelectric point: approximately 4.4
   molecular weight: approximately 88 kDa.
   Michealis-Menton constant: approximately 27 millimoles
   maximum reaction velocity: approximately 27 micromoles per minute per milligram
   Enzymatic activity: greater than 20,000 nanomoles per minute per milligram.

2. The enzyme of claim 1 having the N terminal sequence of SEQ ID NO:1.

3. A glucose oxidase insect salivary enzyme purified and isolated from an insect from the order of Lepidoptera, the super family of Noctuiodea, having the following physicochemical properties:
   action: catalyzing the following reaction:
   glucose+$O_2$→gluconic acid+hydrogen peroxide
   molecular weight: approximately 88 kDa.
   optimum pH: approximately 7.0
   isoelectric point: approximately 4.4
   Michealis-Menton constant: approximately 27 millimoles,
   maximum reaction velocity: approximately 27 micromoles per minute per milligram
   enzyrrmtic activity: greater than 20,000 nanomoles per minute per milligram.

4. The glucose oxidase salivary enzyme of claim 3 having the N-terminal sequence of SEQ ID NO: 1.

5. A glucose oxidase salivary enzyme purified and isolated from an insect of the order of hymenpotra, from the family of *Apis mellifera*, having the following physicochemical properties:
   action: catalyzing the following reaction:
   Glucose+$O_2$→gluconic acid+hydrogen peroxide
   molecular weight: approximately 88 kDa.
   optimum pH: approximately 7.0
   isoelectric point: approximately 4.4
   Michealis-Menton constant: approximately 27 millimoles
   maximum reaction velocity: approximately 27 micromoles per minute per milligram
   enzymatic activity greater than 20,000 nanomoles per minute per milligram.

6. The glucose oxidase salivary enzyme of claim 5, having the N-terminal sequence of SEQ ID NO 1.

7. A method of increasing plant resistance to pathogens comprising the steps of;
   lacerating at least one leaf of said plant;
   applying at least 10 micrograms of an enzynme to the lacerated portion of said leaf;
   wherein said lacerating step is accomplished using a method selected from the group consisting of cutting, puncturing or excising of a small portion of leaf tissue;
   wherein said enzyme comprises a glucose oxidase salivary enzyme isolated and purified from Helicoverpa having the following physiochemical properties:
   action: catalyzing the following reaction:
   glucose+$O_2$→gluconic acid+hydrogen peroxide
   optimum pH: approximately 7.0
   isoelectric point: approximately 4.4
   molecular weight: approximately 88 kDa.
   Michealis-Menton constant: approximately 27 millimoles
   maximum reaction velocity: approximately 27 micromoles per minute per milligram
   Enzymatic activity: greater than 20,000 nanomoles per minute per milligram; and,
      for a time and under conditions that increase a plant's resistance to pathogens.

8. The method of claim 7 wherein said lacerating step consists of excising at least one 0.5 centimeter disk from a leaf of said plant.

* * * * *

UNITED STATES PATENT AND TRADEMARK OFFICE
CERTIFICATE OF CORRECTION

PATENT NO. : 6,303,326 B1
DATED : October 16, 2001
INVENTOR(S) : Gary W. Felton et al.

It is certified that error appears in the above-identified patent and that said Letters Patent is hereby corrected as shown below:

<u>Column 13,</u>
Line 33, "enzyrrmtic" should be -- enzymatic --;

<u>Column 14,</u>
Line 16, "enzynme" should read -- enzyme --.

Signed and Sealed this

Nineteenth Day of March, 2002

Attest:

JAMES E. ROGAN
*Attesting Officer*     *Director of the United States Patent and Trademark Office*